United States Patent
Romero Fanego et al.

(10) Patent No.: US 9,196,107 B2
(45) Date of Patent: Nov. 24, 2015

(54) USE OF RAMAN MARKERS FOR AUTHENTICATING SECURITY DOCUMENTS

(75) Inventors: Juan José Romero Fanego, Madrid (ES); Vicente García Juez, Madrid (ES); José Francisco Fernández Lozano, Madrid (ES); Javier Gamo Aranda, Madrid (ES); Miguel Ángel Rodríguez Barbero, Madrid (ES); Andrés Ruiz Quevedo, Madrid (ES); Israel Lorite Villalba, Madrid (ES)

(73) Assignees: Fábrica Nacional de Moneda y Timbre-Real Casa de la Moneda, Madrid (ES); Consejo Superior de Investigaciones Científicas C.S.I.C., Madrid (ES)

( * ) Notice: Subject to any disclaimer, the term of this patent is extended or adjusted under 35 U.S.C. 154(b) by 95 days.

(21) Appl. No.: 14/123,362

(22) PCT Filed: Jun. 1, 2012

(86) PCT No.: PCT/EP2012/060329
§ 371 (c)(1),
(2), (4) Date: Feb. 7, 2014

(87) PCT Pub. No.: WO2012/164054
PCT Pub. Date: Dec. 6, 2012

(65) Prior Publication Data
US 2014/0176941 A1  Jun. 26, 2014

Related U.S. Application Data (60) Provisional application No. 61/514,688, filed on Aug. 3, 2011.

(30) Foreign Application Priority Data

Jun. 2, 2011 (EP) .................................... 11382183

(51) Int. Cl.
G01J 3/44 (2006.01)
G07D 7/12 (2006.01)
G01N 21/65 (2006.01)
B42D 25/29 (2014.01)

(52) U.S. Cl.
CPC ................ G07D 7/122 (2013.01); B42D 25/29 (2014.10); G01N 21/65 (2013.01); *B42D 2033/20* (2013.01); *B42D 2035/34* (2013.01)

(58) Field of Classification Search
CPC ................ G01N 21/65; G01N 21/658; G01N 2021/656; G01J 3/01; G01J 3/44
USPC .............................................. 356/301, 72–73
See application file for complete search history.

(56) References Cited

U.S. PATENT DOCUMENTS 5,324,567 A  6/1994 Bratchley et al.
5,718,754 A  2/1998 Macpherson et al.
(Continued)

FOREIGN PATENT DOCUMENTS

| EP | 2 319 613 A1 | 5/2011 |
| WO | WO 97/39428 A1 | 10/1997 |
| WO | WO 00/18591 A1 | 4/2000 |
| WO | WO 2010/135351 A1 | 11/2010 |

OTHER PUBLICATIONS

International Search Report dated Aug. 31, 2012 corresponding to International Application No. PCT/EP2012/060329.

*Primary Examiner* — Abdullahi Nur
(74) *Attorney, Agent, or Firm* — Jenkins, Wilson, Taylor & Hunt, P.A.

(57) ABSTRACT

The present invention relates to the use of non deactivable security markers comprising the combination of at least two types of nanoparticles of materials presenting Raman effect, wherein said nanoparticles are in a dispersed state or is forming agglomerates of between 2 and 500 nanoparticles. The invention also relates to security documents, articles or elements incorporating these markers, as well as to a method and system for the detection thereof.

15 Claims, 3 Drawing Sheets

(56) References Cited

U.S. PATENT DOCUMENTS

| | | |
|---|---|---|
| 2002/0025490 A1 | 2/2002 | Shchegolikhin et al. |
| 2006/0038979 A1* | 2/2006 | Natan et al. .................... 356/71 |
| 2007/0165209 A1 | 7/2007 | Natan et al. |
| 2007/0172653 A1* | 7/2007 | Berkland et al. ............. 428/402 |

* cited by examiner

USE OF RAMAN MARKERS FOR AUTHENTICATING SECURITY DOCUMENTS

CROSS-REFERENCE TO RELATED APPLICATIONS

This application is filed under the provisions of 35 U.S.C. §371 and claims the priority of International Patent Application No. PCT/EP2012/060329 filed on Jun. 1, 2012, of U.S. Provisional Patent Application No. 61/514,688 filed on Aug. 3, 2011, and of European Patent Application No. 11382183.9 filed on Jun. 2, 2011. The disclosures of the foregoing international patent application, U.S. provisional patent application, and European patent application are hereby incorporated by reference herein in their respective entireties.

FIELD OF THE INVENTION

The present invention relates to non deactivable security compositions that can be used as carriers of authentication or anti-forgery features in security documents or articles.

BACKGROUND

As demonstrated by the huge number of patents existing in this field, the use of different security elements making the forgery of documents difficult has been extended in recent years. Some of these elements are detectable by human beings, meanwhile other security elements which are incorporated into documents require the use of special tools for detection thereof. These tools include spectroscopic methods such as UV-VIS absorption spectroscopy, fluorescence emission spectroscopy, IR spectroscopy or Raman spectroscopy.

Thus, luminescence pigments or substances have been incorporated into various security documents for certifying the authenticity thereof, the detection or observation of which requires the use of an excitation light in a particular region of wavelengths (for example UV light). Nevertheless, the use of this type of luminescence pigments or substances has some drawbacks including the limited amount of optical transitions (absorptions and emissions) with suitable properties for this application.

Raman spectroscopy in turn has also been described as a suitable method for detecting the authentication of documents. Raman Effect is based on an inelastic scattering of photon produced after impacting light on a material. In other words, an energy transfer between light and the material is produced such that the light coming out from the material has a frequency (or a wavelength or energy) different from that of the incident light. To enable observing this effect, it is necessary to use a strongly monochromatic light generally a laser radiation. The new frequency coming out with the light is directly related to the vibration frequencies of the bonds between the atoms forming the material, and therefore with the typical phonons of the network in the case of a crystal or a glass. Therefore Raman Effect, like infrared spectroscopy, is a vibration effect and in both cases the typical vibrations of the material, either the chemical bonds or the crystal network thereof are measured. This makes Raman effect a powerful tool for determining the structure and/or composition of materials. Raman spectroscopy can be used for example for recognizing drugs or for studying pigments in ancient work of arts, etc, and is very used in chemical and pharmaceutical industry. Nevertheless, not all materials present Raman Effect. Particularly, metals and some materials the crystal structure of which is cubic show no signal. However, the rest of the crystal structures, glasses and even gases and liquids present Raman Effect.

Since the Raman spectrum of each material is unique, different compounds have been incorporated in security elements as markers allowing the authentication thereof. Thus, the use of polydiacetylenes, for example, as active Raman compounds in security inks is described in U.S. Pat. No. 5,324,567. In this document these compounds in the form of particles with a maximum dimension of 40 microns are used. U.S. Pat. No. 5,718,754 in turn describes a pigment which has adsorbed on its surface a compound presenting azo, azomethine, or polycyclic chromophore groups showing Raman spectrum. Other compounds of organic origin used in the form of microparticles as Raman markers are described in US 2002/0025490.

Nevertheless, the use of these compounds as Raman markers does not involve an especially safe authentication system since the proper disclosure of the structure thereof would allow reproducing it, making the system readily forgeable provided that means suitable for the synthesis thereof is provided. Furthermore, when a single Raman material is selected for making an invisible image or a barcode, for example, areas in which there is a high concentration of a material (the active Raman material) which are not in the rest of the document which allows deducing the presence of an image are found and it can further allow knowing the material used using to that end suitable microanalysis techniques.

On the other hand, it is known in the state of the art that materials in the form nanoparticles have properties different from those that are shown in large material (in larger sizes greater than one micron). Thus, the position of the Raman peaks varying with the size of the nanoparticles has been described. In other words, nanoparticles of a particular material with a well defined particle size present a Raman spectrum with well defined peaks in well established positions. This same material but with a different particle size presents a spectrum very similar to the above but shifted in frequencies such that it is easy to distinguish both materials.

Document WO 2010/135351 describes nanoparticles comprising a core formed by an active marker and a metal coat. These nanoparticles can act as optical labels being useful for identifying or quantifying substances or objects and are applied as security measure for preventing forgery of documents, serialization, traceability, etc. Materials used as markers include conjugated polyaromatic compounds, porphyrins, phthalocyanines, metal oxides and ionic liquids. Documents US 2007/165209 and US 2006/038979 refer to method for providing a security element for documents particularly bills comprising applying a label to a portion of the document where said label comprises a metal nanoparticle, a Raman associated active molecule on the surface of the nanoparticle and a encapsulant surrounding said nanoparticle. The mentioned label can also be applied as an ink.

In all these cases, metal element is used as an amplifier of Raman signal without any effect on the spectrum itself therefore they do not involve an improvement as a security system, with the exception of the fact that they allow reducing the amount of active material and thereby increasing the difficulty for duplicating them.

Therefore, there is a clear need to develop new compositions and methods which make forging security documents difficult.

BRIEF DESCRIPTION OF THE INVENTION

The authors of the present invention have observed that the Raman spectrum of the nanoparticles of an organic or inorganic material is modified upon varying the agglomeration state thereof. When the nanoparticles are agglomerated, the frequency at which the peaks appear in the Raman spectrum is different to that found when the nanoparticles are in a dispersed state. Therefore, the dispersed state or the agglomeration state of the nanoparticles allows defining new properties of the security material and can be considered as a new marker for authenticating of the same.

Nanoparticles can be found in a dispersed form or an agglomerate-forming form. Unless the nanoparticles are treated in some particular manner, nanoparticles in solid state generally have a high degree of agglomeration and these agglomerates are hard to brake as they reform spontaneously.

To enable using the agglomeration state of the nanoparticles as Raman marker in security documents one must have control over the size of these agglomerates to allow selecting a specific agglomeration state that is associated with a particular and unique Raman spectrum.

A hardly reproducible security system is provided as it is very complicated to determine whether the nanoparticles are in a dispersed form or are forming agglomerates of a controlled size. It is not only necessary to know the type of nanoparticle used, rather it is also necessary to know if they are in a dispersed form or what is their specific agglomeration state and reproduce it.

It has also been observed that the combination of two types of nanoparticles in a dispersed state or each with a well defined agglomeration state gives rise to a Raman spectrum different from each of them separately. Therefore, said spectrum is particular and can only be given for a specific combination of types of nanoparticles in a dispersed state or with a specific agglomeration state for each of them, therefore the use of this combination even involves an additional improvement in the security of the document since the reproducibility of the combination is yet more difficult.

It has been particularly observed that the dispersed nanoparticles or the agglomerates comprising between 2 and 500 nanoparticles allow defining a Raman spectrum characterized and differentiated for each of them. In other words, there is a unique Raman spectrum for the dispersed state and for each agglomerate size within the referred range. Particularly, changes in energy at which the Raman peaks appear and in the width thereof are produced making them easily distinguishable.

Therefore, a first aspect of the present invention constitutes the use of a combination comprising at least two types of nanoparticles of materials presenting Raman effect wherein each of the at least two types of nanoparticles is in a dispersed state or is forming agglomerates of between 2 and 500 nanoparticles, wherein said agglomerates have a size less than 2 microns for preparing or labeling a security document article or element.

The at least two types of nanoparticles used in the present invention are differentiated in their chemical composition, in their crystal structure, in their shape, in their size and/or in their dispersed or agglomeration state, but they are always conditioned so that they are in a dispersed state or are forming agglomerates of between 2 and 500 nanoparticles.

In a second aspect, the invention relates to a security article, document or element comprising the combination of at least two types of nanoparticles of materials presenting Raman effect wherein each of the at least two types of nanoparticles is in a dispersed state or is forming agglomerates of between 2 and 500 nanoparticles wherein said agglomerates have a size less than 2 microns.

In a third aspect, the invention relates to a method for incorporating a combination of at least two types of nanoparticles as defined previously in a security document or article wherein said incorporation is performed:
  (i) during the manufacturing of the material used to make said article or document; or
  (ii) as part of an additive which is added to said article or document; or
  (iii) on the surface of said article or document, wherein the combination of the at least two types of nanoparticles forms part of a single composition which is incorporated into the security article or document according to any of methods i)-iii), or
wherein each of the at least two types of nanoparticles forms part of an independent composition, the resulting composition combination being that which is incorporated into the security article or document according to any of methods i)-iii).

Likewise, the invention relates to a method for determining the authenticity of a security document, article or element as has been defined previously comprising measuring the Raman spectrum of said security document, article or element to determine the presence of a combination of at least two types of nanoparticles of materials presenting Raman effect wherein each of the at least two types of nanoparticles is in a dispersed state or is forming agglomerates of between 2 and 500 nanoparticles, wherein said agglomerates have a size less than 2 microns.

In another aspect, the invention relates to a system for determining the authenticity of a security document, article or element as has been defined previously, comprising:
  a positioner where the security document, article or element is placed;
  a set of lenses which allows focusing the light originating from an incident laser beam on the part of the document, article or element to be irradiated;
  a multichannel Raman spectrum detector;
  a filter for blocking the laser radiation that reaches the multichannel detector.

DETAILED DESCRIPTION OF THE INVENTION

The use of the combination of at least two types of nanoparticles in which the nanoparticles are in a dispersed form or are forming agglomerates with a controlled size involves a very safe labeling system since the presence of security material can only be confirmed by using a system suitable for obtaining Raman spectrum. The region in which the Raman spectrum of a material appears depends on the excitation radiation wavelength but the very low intensity and proximity to the excitation wavelength thereof make it impossible to distinguish it unless suitable measurement equipment are used.

The combination of at least two types of nanoparticles in a dispersed state or with a specific agglomeration state for each of them provides a well differentiated Raman spectrum giving rise to a defined and reproducible mixture. Said combination of nanoparticles forms a security marker which can be coded. This involves an increase in the complexity of the security marker since it is characterized not only by the composition thereof but also by the dispersed or agglomeration state of the nanoparticles forming it.

Compositions Used in the Invention

The present invention relates in a first aspect to the use of a combination comprising at least two types of nanoparticles of materials presenting Raman effect wherein each of the at least two types of nanoparticles are in a dispersed state or is forming agglomerates of between 2 and 500 nanoparticles wherein said agglomerates have a size less than 2 microns for preparing or labeling a security document, article or element.

In the context of the present invention, the term "nanoparticles" relates to a structure the mean size of which is less than 1 micron, i.e., the mean size thereof is comprised between 1 and 999 nm. The nanoparticles can have a spherical, laminar or fibrous morphology, their main feature being that at least one of their dimensions is nanometric, i.e. less than one micron, preferably less than 100 nm, more preferably less than 50 nm, yet more preferably less than 25 nm. Nevertheless, it must be taken into account that said nanoparticle size is conditioned so that, in the event that the nanoparticles are forming agglomerates, said agglomerates have a size less than 2 microns.

The term "type of nanoparticles" relates to a group of nanoparticles characterized by the chemical composition, crystal structure, shape, size and dispersed or agglomeration state thereof.

As mentioned before, the at least two types of nanoparticles used in the present invention are differentiated in their chemical composition, in their crystal structure, in their shape, in their size and/or in their dispersed or agglomeration state, but they are always conditioned so that they are in a dispersed state or are forming agglomerates of between 2 and 500 nanoparticles.

Preferably, the at least two types of nanoparticles used in the present invention are differentiated in their chemical composition, in their crystal structure, in their size and/or in their dispersed or agglomeration state, but they are always conditioned so that they are in a dispersed state or are forming agglomerates of between 2 and 500 nanoparticles.

The term "dispersed state" is used in the context of the present invention to define nanoparticles which are dispersed, i.e., isolated nanoparticles which are not in direct contact with one another through physical or chemical interactions. Said dispersed state provides a unique Raman spectrum for a type of nanoparticles, regardless of the number of isolated nanoparticles present.

The term "agglomeration state" or "agglomerates" is used in the context of the present invention to define the association of a particular and controlled number of nanoparticles which always comprised between 2 and 500 that are bound through physical processes, i.e., without producing chemical reactions between them. The size of the agglomerates resulting from said association is less than 2 microns, more preferably less than 500 nm, yet more preferably less than 200 nm. Unlike the dispersed state, there is a unique and characteristic Raman spectrum for each agglomerate size, i.e., the Raman spectrum depends on the number of nanoparticles present in each agglomerate.

Therefore, when two types of nanoparticles differentiated by their dispersed or agglomeration state are defined, two types of nanoparticles must be understood, one of which is in a dispersed state and the other is forming agglomerates of between 2 and 500 nanoparticles, or both are forming agglomerates of different size, i.e., agglomerates containing different number of nanoparticles always comprising between 2 and 500.

In a preferred embodiment, one of the at least two types of nanoparticles is forming agglomerates of less than 400 nanoparticles, more preferably of less than 300, more preferably of less than 200, more preferably of less than 150, more preferably of less than 100, more preferably of less than 50, yet more preferably of less than 25.

The term "combination" in the present invention relates to a physical mixture of the at least two types of nanoparticles as have been described previously.

Said combination of the at least two types of nanoparticles can form part of a single composition (known as security composition) or each type of nanoparticles can be incorporated in an independent composition resulting in the combination of at least two compositions (known as security compositions).

Therefore, the term "security compositions" must be understood as a composition comprising the combination of at least two types of nanoparticles as has been defined previously, or a combination of two compositions, each of comprising a type of nanoparticle as has been defined previously.

The combination of the at least two types of nanoparticles can give rise to, among others, the following security compositions:

- a composition comprising two types of nanoparticles, wherein said nanoparticles are in a dispersed state or in the same agglomeration state, they have the same nanoparticle size and the same nanoparticle form but have different chemical composition;
- a composition comprising two types of nanoparticles, wherein said nanoparticles have the same chemical composition, the same crystal structure, the same nanoparticle size and the same nanoparticle form, but they have a different dispersed or agglomeration state;
- a composition comprising two types of nanoparticles, wherein said nanoparticles have the same chemical composition, the same nanoparticle size, the same nanoparticle form and are in a dispersed state or in the same agglomeration state, but they have a different crystal structure;
- the combination of two compositions, each of comprising a type of nanoparticles and wherein said nanoparticles are in a dispersed state or in the same agglomeration state, they have the same nanoparticle size and same nanoparticle form but have different chemical composition;
- the combination of two compositions each of comprising a type of nanoparticles and wherein said nanoparticles have the same chemical composition, the same crystal structure, the same nanoparticle size and the same nanoparticle form but they have different dispersion or agglomeration state;
- the combination of two compositions each of comprising a type of nanoparticles and wherein said nanoparticles have the same chemical composition, the same nanoparticle size, the same nanoparticle form and are in a dispersed state or in the same agglomeration state but they different crystal structure, with the condition that the at least two types of nanoparticles are in a dispersed state or are forming agglomerates of between 2 and 500 nanoparticles in all these compositions or composition combination.

The term "material presenting Raman effect" in turn relates to any type of material either of organic or inorganic origin capable of providing a Raman spectrum characteristic of said material. In other words, it must be a material which allows the inelastic scattering of photons that arrive after light is impacted thereon, such that the light coming out from this material has a frequency different from that of the incident light.

The materials formed by the nanoparticles used in the invention are characterized by presenting a well defined Raman spectrum which is determined both by the composition, crystal structure, shape and size and by the dispersed or agglomeration state thereof.

In a particular embodiment, the material formed by the nanoparticles of the composition of the invention is selected from silicon, metal oxides, hydroxides, carbonates, sulfates, phosphates, silicates, borates, aluminates, heat stable polymers, thermoplastic polymers and polymer resins. Preferably, the material is selected from silicon and metal oxides, more preferably $Co_3O_4$, $Ce_2O_3$, $TiO_2$, $X(WO_3)_4$ or $XNbO_3$, wherein X can be alkaline, alkaline-earth, transition metal or lanthanide elements.

The nanoparticles used in the composition of the invention can be synthesized by different conventional methods in this type of processes known by the person skilled in the art and they include ceramic methods, mechanochemical methods, chemical or electrochemical methods or vapor phase physical or chemical deposition techniques. The size of the particles of the invention can be selected during the synthesis process itself using, for example, suitable surfactants in manufacturing processes by chemical methods or by means of performing controlled grinding processes to reduce the particle size from large materials.

According to an embodiment of the invention, the at least two types of nanoparticles are in a ratio between 1:1 and 20:1 by weight, preferably between 1:1 and 10:1, more preferably between 1:1 and 5:1, even more preferably between 1:1 and 3:1 by weight.

In a preferred embodiment, the nanoparticles of the invention, either in a dispersed form or forming agglomerates of a particular and controlled number of nanoparticles of between 2 and 500, are deposited on a substrate or on larger sized support particles, i.e., of a range greater than the nanometric. The support particles or substrates on which the nanoparticles are deposited must be chemically inert, being unable to react with the mentioned nanoparticles. Said particles or substrates must further be formed by materials that do not present Raman signal in the same frequencies as the nanoparticles.

The technique described in document WO 2010/010220, for example, can be used for the preparation thereof. Said technique allows obtaining dispersed nanoparticles as well as agglomerates with a controlled size such that a unique and characteristic Raman spectrum can be associated to the dispersed state and to each agglomeration state.

Preferably, the nanoparticles are added for dispersing thereof in a ratio less than 5% by weight in relation to the support particles, preferably less than 3% by weight, more preferably between 0.03 and 2% by weight.

In a particular embodiment, the nanoparticles are deposited on support particles, these particles are preferably within the micrometric range. Said particles can be formed by materials of organic or inorganic origin provided that said material does not present Raman signal in the same frequencies as the nanoparticles. Said particles can be formed by materials of inorganic origin such as metal oxides, hydroxides, carbonates, sulfates, silicates, borates or aluminates, by materials of organic origin such as heat stable polymers, thermoplastic polymers or polymer resins, or by materials of metal origin. They are preferably micrometric particles of oxide materials, semiconductors or insulators.

In another particular embodiment, the nanoparticles are deposited on an inert substrate. The substrate used is selected from a material of ceramic type, vitreous type, polymer type, metal type, or compound or hybrid materials. More preferably, it is selected from alumina, single crystal silicon, ceramic glaze, a metal alloy such as kovar or any combination thereof.

In another particular embodiment, the substrate used has the form of fibers. Preferably, said substrates are natural fibers such as cotton fibers, for example.

The nanoparticles, once deposited on any of the mentioned substrates form a coat on said substrate with a thickness preferably less than 100 nm, more preferably less than 50 nm.

In a preferred embodiment of the invention, the at least two types of nanoparticles have the same chemical composition, the same crystal structure, the same nanoparticle size and the same nanoparticle shape but different agglomeration state.

In a yet more preferred embodiment, the at least two types of nanoparticles have the same chemical composition, the same crystal structure, the same nanoparticle size and the same nanoparticle shape but one of the at least two types of nanoparticles are in a dispersed state, and the another of the at least two types of nanoparticles is forming agglomerates comprising between 2 and 500 nanoparticles, more preferably between 10 and 100 nanoparticles.

The use of nanoparticles of a same material, same crystal structure, same nanoparticle shape and same nanoparticle size in two different agglomeration states, or one in a dispersed state and the other in a specific agglomeration state involves a significant increase in the security of the system. Since the Raman spectrum is unique and can only be given for a specific combination of at least two types of nanoparticles with a different agglomeration/dispersed state, said combination can be considered as a good security marker.

A possible method for labeling security documents is the printing of special images such as the frets in dollar bills or barcodes involving a particular code thereon. A substantial improvement of these printings is the use of invisibles inks such as security inks, for example, which act by means of the Raman effect. Nevertheless, when the use of a single material with Raman effect is selected to make one of these invisible images or barcodes, areas in which there is a high concentration of a material (the active Raman material) which is not in the rest of the document which allows deducing the presence of an image are found and it can further allow knowing the material used, using to that end suitable microanalysis techniques.

The security compositions described in this document can be used for generating security inks which allows making invisible images or barcodes.

Thus, the use of a combination of two inks which comprise nanoparticles having the same chemical composition but different crystal structure, different nanoparticle size, different nanoparticle shape or different agglomeration/dispersed state allows having two different visual tones each of them associated to one of these inks which allows generating invisible barcodes or binary images. Furthermore, in this case it is not possible to observe composition variations in the security document, making deducing the presence of an image or a barcode or determining the characteristics of the material whereby it is made once the presence of this image or barcode is known much more difficult if not impossible.

Security Documents, Articles and Elements

In an additional aspect, the present invention relates to a security element comprising the combination of at least two types of nanoparticles as has been defined previously.

According to the present invention, the term security element relates to an element which is integrated into a security document or article for the purpose of authenticating it. The security element can be integrated into the security article or document in its body (such as for example the body of paper, security threads, security fibers, watermarks, tactile effects, cellulose strips, planchettes or other commonly used elements) or in its surface (such as for example holograms added in different bills and credit cards, security inks, plastic sheets or other commonly used elements).

Nevertheless, since the Raman spectroscopy is fundamentally sensitive to the surface region, the incorporation of the security element on the surface of the document or article is preferred.

The security element can be randomly distributed or attached in specific positions of the document or article and gives security features to the document or article containing it, these features being able to be of a very diverse kind provided that their objective is to make the forging of the security documents or articles difficult or to facilitate the authentication thereof.

According to a particular embodiment, the security element is selected, for example, from security paper, security threads, security fibers, security inks, watermarks, tactile effects, cellulose strips, planchettes, holograms, security pigments or substances, plastic sheets and polymer substrates.

These security elements can be prepared from security compositions comprising the combination of the at least two types of nanoparticles defined previously following the common methods known by the person skilled in the art.

In a particular embodiment of the invention, the nanoparticles are deposited in supports with the form of fibers. Thus, it is possible to deposit said nanoparticles on natural fibers, preferably cotton fibers, such that security fibers which are incorporated into the security element as part of the fibers themselves which form the security paper is provided.

In another particular embodiment, the nanoparticles are deposited on support particles which in turn are incorporated into the formulation of an ink thus giving rise to security inks.

In a particular embodiment, the security element is formed by a security composition comprising the combination of at least two types of nanoparticles such as having been defined previously. In another particular embodiment, the security element is formed by the combination of at least two security compositions wherein each of said security compositions comprises one type of nanoparticles as has been defined previously.

In another particular embodiment, the security element is formed by the combination of two security inks wherein each of said security inks comprises one type of nanoparticles as has been defined previously. In this embodiment, the types of nanoparticles comprised in both security inks have the same chemical composition but they have different crystal structure, different nanoparticle size, different nanoparticle shape and/or different dispersed or agglomeration state.

Preferably, the security element is formed by the combination of two security inks wherein said security inks comprise nanoparticles with the same chemical composition, same crystal structure, same shape and size but in one of the at least two inks the nanoparticles are in a dispersed state and in another of the at least two inks the nanoparticles are forming agglomerates of a controlled size of between 2 and 500 nanoparticles.

If the absolutely invisible nanoparticles are deposited on transparent microparticles or even on the particles forming part of the inks used as security elements themselves, images in any part of a document can be printed with them without the possibility of them being detected by simple view or by conventional methods with the exception of those defined in this patent. Furthermore, since the inks used for defining both colors in the binary images and barcodes have the same chemical composition, it is not possible to distinguish the presence of these images by using any other characterization technique. Thus, a particular image can be made on the figure of a bill for example, this image being detectable only by using suitable Raman equipment.

In the particular case of using inks, the security element is not only formed by a material with well defined properties in terms that it presents a specific Raman spectrum, rather also by a particular code, either a two dimensional image, an anagram or a binary code such as a barcode. This method simplifies the detection of the security element since the latter is located in a well defined region of the security document.

Additionally, these security elements can be used to label articles or security documents.

In another aspect, the invention also relates to a security article or document comprising a combination of at least two types of nanoparticles as has been defined previously. Likewise, the invention relates to a security article or document comprising a security element as has been described previously.

According to the present invention, the term security article or document relates to those having particular characteristics which ensure their origin and therefore their authenticity. These security articles or documents include all of those used by public administrations and their public organizations as well as those used in the private sector when they circulate greatly between the group of citizens and companies, and containing identification, authentication or anti-forgery means or devices. Preferably, the security documents or articles are selected from identification documents such as identification cards, passports, passes and the like, and valuable documents such as bills, cheques, stamps, certificates and the like.

Preferably, the security article or document is selected from security paper, identification documents, banknotes, cheques, stamps and stamp-impressed paper, labels and tickets. More preferably, it is a security paper.

The combination of the at least two types of nanoparticles of the invention can be incorporated into the security article or document:

(i) during the manufacturing of the material used to make said article or document; or
(ii) as part of an additive which is added to said article or document; or
(iii) on the surface of said article or document.

In a particular embodiment, the combination of the at least two types of nanoparticles used in the invention can form part of a single security composition which is incorporated into the security article or document according to any one of method i)-iii) described previously.

In another particular embodiment, each of the at least two types of nanoparticles forms part of an independent security composition, the resulting security composition combination being that which is incorporated into the security article or document according to any one of method i)-iii) described previously.

The combination of the invention can be added to the body of paper of the security documents as a dry load forming part of the body of the paper itself. Nevertheless, since the measurement technique is fundamentally sensitive to the surface region, the incorporation thereof on the surface of the document as a hologram or as an inscribed security thread, or forming part of the glue or lacquer, is preferred. It can also be incorporated into polymer films such as polyvinyl alcohol films, for example, which can coat the security article or document. Likewise, the combination can be incorporated into inks used for printing the security document, enabling forming imperceptible part of images, figures, legends, barcodes or elements for tactile labeling.

The deposition of the nanoparticles on microparticles or on a substrate of a suitable size further allows solving the problem where the nanoparticles pass through the pores of the section of the paper since the microparticles or the substrate are retained in the body of paper together with the nanoparticles deposited on the surface thereof due to its large size.

Thus, the sizes of nanoparticle defined in the invention guarantee its incorporation and stay in the paper. Thus, security document or article is provided with the code corresponding to the combination of selected nanoparticles.

In a particular embodiment of the invention, the nanoparticles are deposited in substrates with the form of fibers. Thus, it is possible to deposit said nanoparticles on natural fibers, preferably cotton fibers, such that security fibers are directly incorporated into the security material as part of the fibers themselves which form the paper is provided.

In another particular embodiment, the nanoparticles are deposited on microparticles where the latter in turn are incorporated into the body of the paper in the form of a pigment or are incorporated into the formulation of the ink itself, thus forming security inks as has been mentioned previously for the security elements.

The combinations of nanoparticles of the invention have a particle size described and characterized by not being detectable by simple view when they are integrated into the security document or article. In a particular embodiment, the percentage of the security composition incorporated into the security document or article is less than 5% by weight, preferably less than 1% by weight, and greater than 0.005% by weight of the total weight of the security document or article. This low concentration makes the compositional identification by techniques used such as chemical analysis, X-ray diffraction, spectroscopic techniques or the like difficult. Nevertheless, the identification of the composition does not represent the security marker therein since the specific response is achieved by the combination of nanoparticles with a particular chemical composition, crystal structure, shape and size which are in a well defined agglomeration state or a dispersed state.

The number of different security markers increases with the number of different active Raman materials used which are characterized by their chemical composition as well as by their crystal structure, the shape and size of the nanoparticles, and by their dispersed or agglomeration state; therefore, the number of different security markers that can be generated is virtually limitless. This allows generating encoded security markers such that a particular security marker corresponds to the documents that have been created at a particular time, or for a particular value or a particular purpose, or by a particular organism, therefore making the security documents traceable and further increasing the security thereof.

The security compositions comprising the at least two types of nanoparticles are always active, a security composition not showing the bands corresponding to the Raman spectrum which characterizes them by the application of electromagnetic waves or other external electric, magnetic, light or heat fields not being possible. Thus, it is impossible that a security document can be falsified by not having the features corresponding to the security composition. Likewise, the response of the materials comprised in the security compositions to Raman cannot be modified without the security document which the materials form a insoluble part being destroyed, therefore the security compositions are characterized by being permanent and non deactivable.

The nanoparticles used in the invention are formed by very stable materials, not being sensitive generally to oxidation or hydration processes. Nevertheless, the nanoparticles or the agglomerates can sometimes be coated with layers of inert materials such as alumina, glasses, silicates, or other oxide materials for protecting them from the environment. In the same manner, the nanoparticles could also be coated with polymers or other organic materials to improve their adherence to the fibers of the paper or for their improved transmission in the event that they form part of inks.

The combination of the at least two types of nanoparticles described in the present invention allows efficiently labeling the security articles or documents, presenting a safe coding system based on the intended combination of nanoparticles of materials in a dispersed state or with a particular agglomeration state, showing a Raman effect depending on their composition, crystal structure, shape, size and dispersed or agglomeration state thereof which gives rise to a virtually limitless number of possible unique security markers. The security compositions described are permanent, non deactivable and have an encoded response which requires the use of a detection system designed for such purpose.

Authentication Method

In another aspect, the invention relates to a method for determining the authenticity of a security document or article which comprises measuring the Raman spectrum of said security document or article to determine the presence of the security marker, i.e., to determine the presence of a combination of at least two types of nanoparticles of materials presenting Raman effect wherein each of the at least two types of nanoparticles are in a dispersed state or are forming agglomerates of between 2 and 500 nanoparticles.

The at least two types of nanoparticles are differentiated in their chemical composition, in their crystal structure, in their shape, in their size and/or in their dispersed or agglomeration state, but they are always conditioned so that they are in a dispersed state or are forming agglomerates of between 2 and 500 nanoparticles.

In a particular embodiment, the invention relates to a method for determining the authenticity of a security document or article comprising the combination of at least two types of nanoparticles of materials presenting Raman effect wherein each of the at least two types of nanoparticles are in a dispersed state or are forming agglomerates of between 2 and 500 nanoparticles, which comprises:

(a) irradiating the security document or article with monochromatic laser radiation; and
(b) measuring the Raman spectrum thereof.

The monochromatic laser radiation that reaches the security document or article is dispersed by the latter, particularly by the security marker or composition contained in said document or article comprising the combination of at least two types of nanoparticles of materials presenting Raman effect wherein each of the at least two types of nanoparticles has a predetermined agglomeration state and comes with a frequency different from that of the incident light. The resulting Raman spectrum is therefore formed by peaks shifted with respect to the signal of the laser by a frequency corresponding with a mode of vibration of the bonds of the material forming the nanoparticles in their dispersed state or in a specific agglomeration state.

Figure 1:
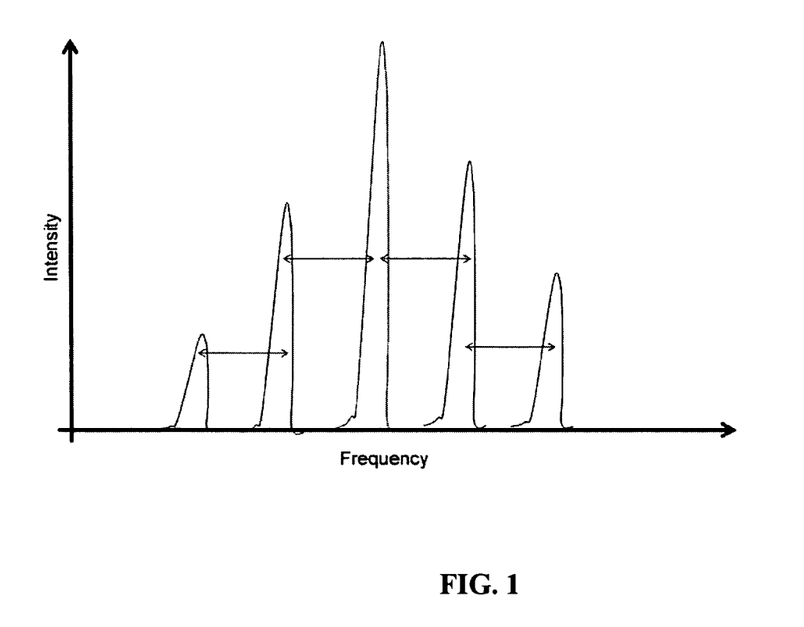
FIG. 1 show the scheme of a Raman spectrum

In the simplest possible case, when there is only one mode of vibration in the material, the laser peak is obtained at a particular wavelength and Raman peaks shifted with respect to said wavelength by an amount corresponding to an integer times the vibration frequency of the material as depicted in FIG. 1 are obtained.

In this figure, the intensity peak originating from the laser beam is located in the center of the image. Two sets of peaks are observed at both sides of the laser peak. These peaks are shifted from the laser peak by one or two times the frequency of the mode of vibration of the material. The peaks which are on the right of the laser at a lower frequency (or energy) are know as Stokes peaks, meanwhile those on the its left are the anti-Stokes peaks. The Stokes peaks correspond to the case in which phonons are emitted to the mass, i.e., the collision of the laser beam with the mass produces vibrations in the material and therefore the dispersed laser has a higher energy, this being coincident with the energy of the vibrations generated. The anti-Stokes peaks are in turn due to an interaction of the laser light with the material where the dispersed radiation shows energy higher than that of the incident beam, corresponding with one of the vibrations of the material. The anti-Stokes peaks are way less probable than Stokes peaks, therefore they show less intensity.

Therefore, once obtaining a security document or article comprising the combination of at least two types of nanoparticles of materials presenting Raman effect wherein each of the at least two types of nanoparticles is in a dispersed state or has an agglomeration state controlled and predetermined for each of them, a monochromatic laser beam is impacted thereon or on a specific area thereof where said combination has been located and the Raman spectrum thereof is measured. Said Raman spectrum is unique and particular for the combination of the at least two types of nanoparticles contained in said security document or article and particularly for the dispersed state or the specific agglomeration state for each type of nanoparticles and it is therefore considered as the reference Raman spectrum for use thereof in the authentication of security documents or articles.

Therefore, in a particular embodiment, the method for determining the authenticity of a security document or article as has been defined previously, comprises:
 a) irradiating the security document or article with monochromatic laser radiation;
 b) measuring the Raman spectrum after impacting the mentioned monochromatic laser light thereon;
 c) comparing the Raman spectrum obtained in step b) with a reference Raman spectrum corresponding to a security document or article which includes a composition comprising the combination of at least two types of nanoparticles of materials presenting Raman effect wherein each of the at least two types of nanoparticles is in a dispersed state or has a predetermined agglomeration state.

The authenticity of the security document or article is confirmed after verifying whether the Raman spectrum obtained in step b) coincides with the reference Raman spectrum of the security marker, or if it is within pre-established limits. Therefore, in a particular embodiment, the authentication method of the invention comprises an additional step of verifying if the Raman spectrum obtained in step b) coincides with the reference Raman spectrum of the security marker or if it is within pre-established limits.

According to another particular embodiment, the Raman spectrum obtained after impacting a monochromatic laser light on the security document or article represents a codification.

Detector

To obtain the Raman spectrum, a detection system comprising a monochromatic radiation source such as a folded Nd:YAG laser, for example, which emits at a wavelength of 532 nm can be used. Since the intensity of the Raman lines is very small, several orders of magnitude smaller than the fluorescence emission intensity for any material and much less intense than that of the incident laser light, it is necessary to use filters which allow blocking the laser radiation. Additionally, the detection system comprises a monochromator for collecting the intensity of the Raman signals at different frequencies or wavelengths, as well as a suitable optical system.

In a particular embodiment, the detection system for detecting the Raman spectrum is compact, ensuring that all the elements are well aligned. To that end, a microscope can be used. Thus, the excitation laser light impacts through a microscope lens and the dispersed signal is collected using the same objective. By using a slightly microscope lens with little magnification (5× or 10×) the Raman spectrum of a region of approximately 1 mm in diameter can be measured. This way for obtaining the Raman spectrum is suitable for the cases in which the nanoparticles are located in a specific region of the security document or article. In the event that said nanoparticles are not located in a specific region, a shift system can be included on said security document or article such that the nanoparticles arranged randomly thereon can be located.

In a preferred embodiment, the detection system for detecting the Raman spectrum comprises a multichannel detector. Detectors of this type allow obtaining the Raman spectrum only once thus preventing the need of performing a frequency or wavelength scan over time which facilitates the review of the Raman spectrum, locating the required Raman peaks in very short times. Therefore, the use of this type of detectors allows authenticating security documents at high speeds.

Therefore, in a particular embodiment, the system for determining the authenticity of a security document, article or element as has been defined previously comprises:
 a positioner wherein the security document, article or element is placed;
 a set of lenses which allows focusing the incident laser light on the part of the document, article or element to be irradiated;
 a multichannel Raman spectrum detector;
 a filter for blocking the laser radiation coming directly from the laser emitter source that reaches the multichannel detector.

In a preferred embodiment, the multichannel detector is a detector known commonly as a CCD.

In another particular embodiment, this system further comprises a device which allows comparing the Raman spectrum obtained with the reference Raman spectrum and thus verifying if the document, article or element analyzed comprises the security marker.

In the event that the security marker described in this patent is used for making binary images or barcodes, the detection system comprises an optical focusing system, a suitable imaging system, and two filters which only allow the passing of the wavelength of the Raman peak corresponding to each of the inks. In this event, as the image is in a well-defined region of the security document the measurement is taken only in this region.

EXAMPLES

Example 1

Use of a Combination of Dispersed Mullite Nanoparticles and Agglomerate Bismuth Molibdate as Security Markers Applied on the Surface in Security Paper to Print Legal Tender Notes

Characteristics of the Nanoparticles Suspension:
  Mullite nanoparticles with acicular shape of 50 nm in diameter and 300 nm in length. The nanoparticles are dispersed. The nanoparticles are characterized with a Raman peak at 970 cm−1.
  Bismuth molibdate nanoparticles with spherical morphology and 20 nm in diameter in an agglomeration state of 200 nm characterized with two Raman peaks at 712 and 846 cm−1.
  The aqueous suspension of particles possess a solid content of 15 wt % in which 5 wt % are mullita nanoparticles and 10 wt % are bismuth molibdate nanoparticles.

Material

A gravure printing machine manufactured by Panday-Graph, a gravure cylinder manufactured by Ziraba, natural cellular-based fibrous paper manufactured in a round paper machine in the Fabrica Nacional de Moneda y Timbre (FNMT), long-lasting varnish and crosslinker manufactured by Sicpa and a dispersion of mullite nanoparticles and bismuth molibdate in an aqueous solution is used.

Characteristics of the Installations and Materials Used

Conditions of the printing machine on each side of the paper:
  Drying tunnel temperature: 145° C.
  Machine speed: 90 m/min
  Suction speed: 2500 rpm
  Blowing speed: 2400 rpm
  Residual moisture of the paper after drying: 6.1-6.8%
Conditions of the Gravure Cylinder
  Type of etching: chemical
  Lineature: 60 line/cm
  Cell depth: 54 microns
  Table: 910 mm
  Diameter: 200 mm
Conditions of the Varnish and Crosslinker:
  Commercial name of the varnish: Primer 803696W
  Commercial name of the crosslinker: First additive 370010
  Viscosity of the varnish after adding crosslinker: 20 s CP4
  Viscosity of the varnish for application: 18 s CP4
Characteristics of the Paper:
  Fibrous composition: 100% cellulose
  Grammage: 90 g/m$^2$
  Grammage after the varnishing process: 96 g/m$^2$
  Thickness: 115 microns
  Bendtsen smoothness on the felt side: <700 ml/min
  Bendtsen smoothness on the fabric side: <800 ml/min
  Bendtsen porosity: <20 ml/min
  Bendtsen porosity after creasing: <140 ml/min
  Cobb value: 40-70 g/cm$^2$
  Ash: <3%
  Opacity: 84%

Embodiment Method

Once the printing machine is started up to reach the established machine conditions, the gravure cylinder is placed, the reel of paper is placed on the unwinding shaft and the web of paper is distributed in the machine circuit, the varnish is mixed with the crosslinker in a proportion of 1.5% by weight of the latter over the former, under gentle stirring conditions in the actual 20 kg drum of varnish.

100 ml of the aqueous dispersion of the combination of particles referred above are added to this mixture. Once the perfect dispersion of the components is assured, the content of the drum is pumped to the inkwell of the printing machine. The paper is positioned on the printing cylinder starting the application of the varnish on the entire width of the web of paper on one of the sides, controlling the final moisture of the paper, viscosity of the varnish and the machine conditions throughout the entire printing process. Once the paper is wound at the machine outlet, the reel is taken off the winder and is placed in the unwinder in the appropriate unwinding direction to print the varnish on the opposite side. After the process ends the reel is left at rest in a minimum development time of 24 hours at room temperature (23° C. and 50% RH).

Example 2

Use of a Mixture of Cerium Oxide Nanoparticles and Titanium Dioxide Nanoparticles as Security Markers Applied in Security Paper Mass Intended for Printing Passports

The characteristics of the nanoparticles suspension are:
  Cerium oxide nanoparticles, $CeO_2$, with spherical morphology of nm in diameter. The cerium oxide nanoparticles are dispersed. The nanoparticles are characterized by a Raman peak at 465 cm$^{-1}$.
  Titanium dioxide nanoparticles, $TiO_2$, in the crystalline form of anatase with spherical morphology and average nanoparticles size of 12.5 nm. The titanium dioxide nanoparticles form agglomerates of ca. 200 nm in diameter. The titanium dioxide nanoparticles are characterized by a main Raman peaks at 145 cm$^{-1}$.
  The aqueous suspension of particles possess a solid content of 10 wt % in which 5 wt % are cerium oxide nanoparticles and 5 wt % are titanium dioxide nanoparticle agglomerates.

Material

A round paper machine and an aqueous dispersion of cellulose fibers suitably bleached and refined in previous production processes are used.

Embodiment Method

The aqueous dispersion of cellulose fibers along with different chemical products such as anti-foaming agents, charge retention agents, color fixing agents, mineral fillers (e.g. titanium dioxide or alumina silicate), pigment dyes, ion and pH regulators and dry resistance resins (e.g. carboxymethyl cellulose), forms the base pulp for manufacturing paper with a consistency or concentration around 3% by weight with respect to the amount of water used with pH between 7 and 8.

The combination of nanoparticles functionalized to be cationic and to have the capacity to form covalent bonds with the oxygen atoms of the carboxyl groups of the cellulose fibers is also in an aqueous dispersion in a 1000 kg dilution tank.

The metering of the aqueous dispersion of the referred nanoparticles towards the machine head vat first causes an electrostatic attraction between said dispersed cerium oxide nanoparticles or agglomerates of titanium dioxide nanoparticles and the anionic fibers to later form the indicated covalent bond.

Wet resistance resin based on polyamide-epichlorohydrin which is also strongly cationic and has the possibility to form covalent bonds similar to that indicated is subsequently added to the paper pulp, and such bonds are formed with as many cellulose fibers are left with this option and it also forms such bonds with itself to form the polymer lattice necessary to give the paper the wet resistance level that is specified.

This entire mass of cellulose fibers and chemical additives subsequently arrive from the machine head ink to the round shape where the layer of paper forming the final sheet of paper after the pressing, drying, gluing and subsequent drying and calendering processes is formed.

The paper manufactured by these means is subsequently used for printing passports.

Example 3

Use of a Mixture of Cerium Oxide Nanoparticles and Titanium Dioxide Nanoparticles as Security Markers Applied in Silk-Screen Printing Ink with an Iridescent Web in Security Paper for Security Labels The characteristics of the Nanoparticles Mixture are:
Cerium oxide nanoparticles, $CeO_2$, with spherical morphology of 70 nm in diameter. The cerium oxide nanoparticles are dispersed. The nanoparticles are characterized by a Raman peak at 465 $cm^{-1}$.
Titanium dioxide nanoparticles, $TiO_2$, in the crystalline form of anatase with spherical morphology and average nanoparticles size of 12.5 nm. The titanium dioxide nanoparticles are dispersed on $Al_2O_3$ microplateles of 6 μm in diameter and 1 μm in thickness. The titanium dioxide nanoparticles are characterized by a main Raman peaks at 143 $cm^{-1}$.
The mixtures of nanoparticles comprise 20 wt % of cerium dioxide and 80 wt % of titanium dioxide nanoparticles on alumina microparticles. The weight ratio of titanium dioxide nanoparticles and alumina nanoparticles is 1:9. In the mixture a dry nanodispersion procedure is adequate to obtain the characteristics.

Material

A silk-screen printing machine manufactured by Stork, a silk screen manufactured by Stork, natural cellular-based fibrous paper manufactured in a round paper machine in the FNMT, iridescent ink, anti-foaming agent and crosslinker manufactured by Sicpa and a mixture of cerium oxide nanoparticles and titanium dioxide nanoparticles is used.

Characteristics of the Installations and Materials Used

Conditions of the Printing Machine on Each Side of the Paper:
  Drying tunnel temperature: 145° C.
  Machine speed: 70 m/min
  Suction speed: 2500 rpm
  Blowing speed: 2400 rpm
  Residual moisture of the paper after drying: 6.5%
Conditions of the Silk Screen
  Reference: RSI900
  Development: 25⅜"
  Mesh: 105
  Open area: 15%
  Thickness: 105 microns
  Width: 910 mm
Conditions of the Iridescent Ink and Additives:
  Commercial name of the ink: Silk-screen printing ink 5WR1241
  Commercial name of the anti-foaming agent: Additive 880775
  Commercial name of the crosslinker: Additive 370010
  Viscosity of the ink after adding crosslinker: 20 s CP4
  Viscosity of the printing ink: 18 s CP4
Main Conditions of the Paper:
  Fibrous composition: 100% cotton cellulose
  Grammage: 90 $g/m^2$
  Grammage after the varnishing process: 96 $g/m^2$
  Thickness: 115 microns
  Bendtsen smoothness on the felt side: <700 ml/min
  Bendtsen smoothness on the fabric side: <800 ml/min
  Bendtsen porosity: <20 ml/min
  Bendtsen porosity after creasing: <140 ml/min
  Cobb value: 40-70 $g/cm^2$
  Ash: <3%
  Opacity: 84%

Embodiment Method

Once the printing machine is started up to reach the established machine conditions, the silk screen is placed, the reel of paper is placed on the unwinding shaft and the web of paper is distributed in the machine circuit, the ink is mixed with the crosslinker in a proportion of 1.5% by weight of the latter over the former, under gentle stirring conditions in the actual 20 kg drum of ink. 100 ml of the mixture of the referred nanoparticles and anti-foaming agent are added to this mixture as needed should foam occur. Once the perfect dispersion of the components is assured, the content of the drum is pumped to the inkwell of the printing machine. The paper is positioned on the printing silk screen starting the printing of the ink through the holes of the screen according to the graphic design established therein on one of the sides, controlling the final moisture of the paper, viscosity of the ink and the machine conditions throughout the entire printing process.

Example 4

Use of a Mixture of Cerium Oxide Nanoparticles and Sodium Potassium Niobate Nanoparticles as Security Markers Applied on the Surface of the Security Paper Intended for Printing Passports The characteristics of the nanoparticles suspension are:
Cerium oxide nanoparticles, $CeO_2$, with spherical morphology of 70 nm in diameter. The cerium oxide nanoparticles are dispersed. The nanoparticles are characterized by a Raman peak at 465 $cm^{-1}$.
Sodium potassium niobate nanoparticles, $K_{0.5}Na_{0.5}NbO_3$, with platelet type morphology and average size of 80 nm. The sodium potassium niobate nanoparticles form irregular agglomerates of ca. 300 nm in average diameter. The sodium potassium niobate nanoparticles are characterize by a main Raman peaks at 620 $cm^{-1}$.

The aqueous suspension of nanoparticles possess a solid content of 25 wt % in which 5 wt % are cerium oxide nanoparticles and 20 wt % are sodium potassium niobate nanoparticles.

Material

A round paper machine and an aqueous dispersion of cellulose fibers suitably bleached and refined in previous production processes are used.

Embodiment Method

The aqueous dispersion of cellulose fibers along with different chemical products such as anti-foaming agents, charge retention agents, color fixing agents, mineral fillers such as titanium dioxide or alumina silicate, pigment dyes, ion and pH regulators and dry resistance resins such as carboxymethyl cellulose, forms the base pulp for manufacturing paper with a consistency or concentration around 3% by weight with respect to the amount of water used with pH between 7 and 8.

Wet resistance resin based on polyamide-epichlorohydrin which is also strongly cationic and has the possibility to form covalent bonds similar to that indicated is subsequently added to the paper pulp and such bonds are formed with as many cellulose fibers are left with this option and it also forms such bonds with itself to form the polymer lattice necessary to give the paper the wet resistance level that is specified. This entire mass of cellulose fibers and chemical additives subsequently arrive from the machine head ink to the round shape where the layer of paper is formed after the pressing and drying processes.

After drying, the paper is moved to the gluing area where it is immersed in a tray that contain a dilution of gluing agents based on polyvinyl alcohol (reference Airvol 103 manufactured by Air Products & Chemical) where 100 ml of aqueous dispersion of the referred nanoparticles, suitably functionalized to have the capacity to form covalent bonds with the oxygen atoms of the hydroxyl groups of the gluing agent, has been added for every 100 liters of gluing agent. The paper is subsequently dried and calendered until obtaining absolute moisture of the paper of 5%. The paper manufactured by these means is subsequently used for printing passports.

Example 5

Use of Dispersed Cerium Oxide and Titanium Dioxide Nanoparticles as Security Markers Applied in the Coated Layer of Paper Intended for Printing Self-Adhesive Security Labels The characteristics of the nanoparticles mixture are:
Cerium oxide nanoparticles, $CeO_2$, with spherical morphology of 20 nm in diameter. The cerium oxide nanoparticles are disperse and anchor on layered type kaolin microparticles with diameter of 1-2 μm and thickness of 200-400 nm. The cerium dioxide nanoparticles are characterized by a Raman peak at 464 $cm^{-1}$.
Titanium dioxide nanoparticles, $TiO_2$, in the crystalline form of anatase with spherical morphology and average nanoparticles size of 12.5 nm. The titanium dioxide nanoparticles are dispersed and anchor on layered type kaolin microparticles with diameter of 1-2 μm and thickness of 200-400 nm. The titanium dioxide nanoparticles present a main Raman peaks at 143 $cm^{-1}$.

The mixtures of nanoparticles comprise 3 wt % of cerium dioxide and 3 wt % of titanium dioxide nanoparticles and 94 wt % of kaolin microparticles. In the mixture a dry nanodispersion procedure is adequate to obtain the characteristics of the mixture. The mixture is incorporate in an aqueous media to obtain a suspension of the nanoparticles disperse on the microparticles with a solid content of 40 wt %.

Material

A knife coating machine which is supplied with a coating slip previously prepared according to the following specially indicated formula for a use of the coated paper in offset printing techniques for self-adhesive security labels was used.

Characteristics of the Installations and Materials Used

Mineral Fillers:
   80% calcium carbonate (Ref Albacar HO Slurry manufactured by Specialty Minerals) and 20% kaolin (reference Supragloss 95 manufactured by Imerys) to obtain 50 parts of the slip.
Synthetic Binder:
   10 parts butadiene styrene latex (reference Styronal D-517 manufactured by BASF).
Synthetic Co-Binder:
   2 parts (reference Acronal 700 L manufactured by BASF).
Thickener:
   1 part carboxymethyl cellulose.
Insolubilizing Agent:
   1 part (reference Basocoll OV manufactured by BASF).
Additives:
   1 part sodium hydroxide.
Aqueous Dispersion of Dispersed Cerium Oxide and Titanium dioxide nanoparticles:
   1 part.
Water:
   The rest up to 100 parts.
Self-Adhesive Paper to be Coated:
   Total grammage: 200 $g/m^2$
   Grammage of siliconized support: 82 $g/m^2$
   Grammage of adhesive: 20 $g/m^2$
   Fibrous composition of the front side: 100% cellulose from mechanical pulp.
Conditions of the Coating Machine:
   Drying tunnel temperature: 145° C.
   Machine speed: 150 m/min
   Residual moisture of the paper after drying: 6.5%
Characteristics of the Coated Paper:
   Total grammage: 220 $g/m^2$
   Grammage of coated layer: 20 $g/m^2$
   Bekk smoothness on the coated side: 200 sec
   Ash: 20%
   Opacity: 84%

Embodiment Method

Once the coating machine is started up to reach the established machine conditions, the reel of paper is placed on the unwinding shaft and the web of paper is distributed in the machine circuit, the coating slip is metered into the tray of the knife coater and the coating process begins according to the established machine conditions until finishing the reel.

After the coating process, the reel of paper is calendered until reaching the smoothness established and is cut to the format necessary for the subsequent process for sheet or reel printing of the security labels.

Example 6

Use of Cobalt Oxide Nanoparticles as Security Markers Applied in the Security Fiber Mass Intended for Inclusion in Security Paper Mass The Characteristics of the Cobalt Oxide Nanoparticles are:
Cobalt oxide nanoparticles, $Co_3O_4$, with spherical morphology of 25 nm in diameter. The nanoparticles are agglomerated in agglomerates with diameter of 400 nm. The cobalt oxide agglomerates of nanoparticles are characterized by a Raman peak at 662 $cm^{-1}$.
The cobalt oxide nanoparticles are dispersed and anchor on the alumina platelet microparticles described in the example 3. The ratio of cobalt oxide nanoparticles and alumina microplatelet is 1:99. The disperse cobalt oxide nanoparticles present a Raman peaks at 695 $cm^{-1}$.
The mixtures of nanoparticles comprise 10 wt % of agglomerate cobalt oxide nanoparticles and 90 wt % of disperse cobalt oxide nanoparticlese. The mixture is incorporate in an aqueous media to obtain a suspension of the cobalt oxide nanoparticle in the agglomerate state and the dispersed nanoparticles on the alumina microparticles with a total solid content of 40 wt %.

This example uses a plastic material extrusion machine made up of a metering hopper with circular section where the chips of polymer material are metered, a piston meter where the cobalt oxide nanoparticles are metered, a single screw extruder with Maddock type mixer and spinning head, an air cooling system, a fiber tempering or tensing system and a cutter. The main process parameters in use and the configuration parameters of this machine are indicated below.

Configuration of the Screw of the Extruder:
  Screw diameter: 5 cm
  Screw length in the feeding area: 50 cm
  Screw length in the compression area: 30 cm
  Screw length in the metering area: 20 cm
  Angle of the blades: 17.65°
  Thread pitch: 5 cm
  Gap between cylinder and screw: 0.5 cm
  Depth of the metering channel; 0.25 cm
  Depth of feeding channel 0.75 cm
  Outer diameter of the cylinder: 7.01 cm
  Inner diameter of the cylinder: 5.01 cm
  Length of the mixer: 10 cm
  Number of holes of the spinning head: 50
  Diameter of the holes: 0.15 mm
Process Parameters of the Extruder:
  Range of temperatures along the cylinder: 120-185°
  Fiber flow rate at the outlet of the spinning head: 10 l/h
  Output speed: 3.14 m/s (7.5 kg of fiber/hour)
Characteristics of the Polymer Material:
  Composition: polypropylene manufactured by LyonDell-Basell (ref.: HM560R)
  Chip density: 0.91 $g/cm^3$
  Melting temperature: 145° C.
  Fluidity Index: 25 g/10 min (230° C./2.16 kg)
Characteristics of the Security Fibers:
  Thickness: 0.02 mm
  Length: 3 mm Implementation Method:
Once the extrusion machine is started up in the indicated configuration and process parameters, coat to reach the established machine conditions, the heated hopper is fed with the polypropylene chips. The markers with cobalt oxide nanoparticles are introduced by using a vertical piston meter located between the feeding area and the compression area of the extruder. The material is gradually mixed and pressed as it moves along the screw starting with an atmospheric pressure in the hopper and increasing until the outlet through the nozzle. Before reaching the mixer, the components pass through a mesh or filter. After going through the mixer the material is subjected to maximum pressure and passes through a spinning head provided with small holes where the fibers are produced.

Once the fibers are obtained, they must be cooled by means of an air current and are subsequently collected by a drive roller feeding the tensing unit. In this unit the fibers align their crystalline structure in the direction of the axis of the filament enabling their lengthening which is produced through the action of a roller which is at the end of the drying chamber and which rotates at a speed 4 times faster than that of the outlet of the spinning head.

Then another roller drives the fibers to the cutting machine where a set of stationary blades cuts the fibers into the specific length.

Example 7

Use of a Mixture of Iron Nanoparticles as Security Markers Applied in Silk-Screen Printing Ink of Polymeric Substrates for Identification Cards The characteristics of the iron oxide nanoparticles are:
Iron oxide nanoparticles of magnetite structure, $Fe_3O_4$, with spherical morphology of 20 nm in diameter are agglomerated in agglomerates with diameter of 200-400 nm. The magnetite iron oxide agglomerates of nanoparticles are characterized by main Raman peaks at 300, 532 and 662 $cm^{-1}$.
Iron oxide nanoparticles, hematite $\alpha$-$Fe_2O_3$, with spherical morphology of 15 nm in diameter are agglomerated in agglomerates with diameter of 300 nm. The maghemite iron oxide agglomerates of nanoparticles are characterized by main Raman peaks at 225, 293, 412 and 613 $cm^{-1}$.
The aqueous dispersion of nanoparticles comprises 10 wt % of agglomerate magnetite iron oxide nanoparticles and 10 wt % of agglomerate hematite iron oxide nanoparticles.

This example uses a silk-screen printing machine jointly manufactured by Stork and Thieme with ultraviolet drying, a Rotaplate silk screen manufactured by Stork, polyester-based polymeric substrate, silk-screen printing ink manufactured by Sicpa and a dispersion of iron oxide nanoparticles in a liquid solution.

The main characteristics of the installations and materials indicated are described below:
Conditions of the Printing Machine on Each Side of the Paper:
  Machine speed: 4000 sheets/hour
  Conditions of drying: 60%
Conditions of the Silk Screen Rotaplate 125W
  Mesh: 125 hpi
  Thickness: 120 microns
  Open area: 43%
  Diameter: 140 microns Conditions of the Iridescent Ink and Additives:
  Commercial name of the ink: Silk-screen printing ink 3Z1Q09
  Viscosity of the printing ink: 120 s CP4
Main Conditions of the Polymeric Substrate:
  Composition: polyester manufactured by PPG Industries (Ref.: Teslin SP 1000)
  Thickness: 200 microns
Implementation Method:
  Once the printing machine is started up to reach the established machine conditions, the silk screen is placed and the substrates of polyester are positioned, a mixture of silk-screen printing ink to which 100 ml of the aqueous dispersion of iron oxide nanoparticles have been previously added is pumped to the inkwell. The printing of the ink through the holes of the screen according to the graphic design established therein on one of the sides, controlling the viscosity of the ink and the machine conditions throughout the entire printing process is subsequently started.

Example 8

Use of Dispersed Cerium Oxide and Titanium Dioxide Nanoparticles as Security Markers Applied in the Coated Layer of Paper Intended for Printing Postal Mail Stamps The characteristics of the nanoparticles are those mentioned in example 5.

Material

A filmpress coating machine which is supplied with a coating slip previously prepared according to the following formula such that the type and characteristics of the coating obtained is specially indicated for a use of the coated paper in gravure printing techniques for postal mail stamps was used.

Characteristics of the Installations and Materials Used

Mineral Fillers:
  50 parts kaolin (reference Supragloss 95 manufactured by Imerys).
Synthetic Binder:
  12 parts butadiene styrene latex (reference L-8000 manufactured by EOC Polymers).
Synthetic Co-Binder:
  2 parts (reference Acronal 700 L manufactured by BASF).
Thickener:
  1 part of carboxymethyl cellulose.
Insolubilizing Agent:
  1 part (reference Basocoll OV manufactured by BASF).
Additives:
  1 part sodium hydroxide.
Aqueous Dispersion of Particles of Inorganic Oxide materials (Combinations 1-4):
  1 part.
Water:
  The rest up to 100 parts.
Paper Support to be Coated:
  Total grammage: 90 g/m$^2$
  Thickness: 120 microns
  Fibrous composition: 100% cellulose from mechanical pulp Conditions of the Coating Machine:
  Drying tunnel temperature: 150° C.
  Machine speed: 170 m/min
  Residual moisture of the paper after drying: 5.5%
Characteristics of the Coated Paper:
  Total grammage: 110 g/m$^2$
  Grammage of coated layer: 20 g/m$^2$
  Bekk smoothness on the coated side: 1800 sec
  Ash: 15%
  Opacity: 80%

Embodiment Method

Once the coating machine is started up to reach the established machine conditions, the reel of paper is placed on the unwinding shaft and the web of paper is distributed in the machine circuit, the coating slip is metered into the tray for supplying the cylinders in contact with the paper and the coating process begins according to the established machine conditions until finishing the reel. After the coating process, the reel of paper is calendered until reaching the established smoothness and is cut to the format necessary for the subsequent process for sheet or reel printing of postal mail stamps.

Example 9

Use of a Mixture of Dispersed Cerium Oxide Nanoparticles, Titanium Dioxide Nanoparticles and Bismuth Molibdate Nanoparticles as Security Markers Applied in the Gummed Layer of Paper Intended for Printing Gummed Tax Stamps or Security Labels The characteristics of the nanoparticles mixture are:
Cerium oxide nanoparticles, $CeO_2$, with spherical morphology of 20 nm in diameter. The cerium oxide nanoparticles are disperse and anchor on layered type kaolin microparticles with diameter of 1-2 µm and thickness of 200-400 nm. The cerium dioxide nanoparticles are characterized by a Raman peak at 464 cm$^{-1}$.
Titanium dioxide nanoparticles, $TiO_2$, in the crystalline form of anatase with spherical morphology and average nanoparticles size of 12.5 nm. The titanium dioxide nanoparticles are dispersed and anchor on layered type kaolin microparticles with diameter of 1-2 µm and thickness of 200-400 nm. The titanium dioxide nanoparticles present a main Raman peaks at 143 cm$^{-1}$.
Bismuth molibdate nanoparticles with spherical morphology and 20 nm in diameter in an agglomeration state of 200 nm characterized with two Raman peaks at 712 and 846 cm−1.
The mixtures of nanoparticles comprise 5 wt % of cerium dioxide, 5 wt % of bismuth molibdate nanoparticles and 2 wt % of titanium dioxide nanoparticles and 88 wt % of kaolin microparticles. In the mixture a dry nanodispersion procedure is adequate to obtain the characteristics of the mixture. The mixture is incorporate in an aqueous media to obtain a suspension of the nanoparticles disperse on the microparticles with a solid content of 35 wt %.

Material

A filmpress coating machine which is supplied with a slip of previously conditioned re-wettable gum which is specially indicated for the use of gummed paper for offset printing techniques for gummed tax stamps or security labels. The slip of re-wettable gum used is based on polyvinyl acetate, reference A-4524 manufactured by Henkel Adhesives & Technologies was used.

Characteristics of the Installations and Materials Used 1 liter of aqueous dispersion of the referred mixture of nanoparticles and 1400 grams of green food dye with reference Verde Carta DAM Liquido manufactured by Clariant previously prepared by mixing 1 part of the dye indicated with 3 parts water are added for every 1000 kg tank of gum slip.

Characteristics of the Paper Support to be Gummed:
Total grammage: 95 g/m$^2$
Thickness: 98 microns
Fibrous composition: 100% cellulose from mechanical pulp.

Conditions of the Coating Machine:
Drying tunnel temperature: 130° C.
Machine speed: 140 m/min
Residual moisture of the paper after drying: 5.5%

Characteristics of the Gummed Paper:
Total grammage: 105 g/m$^2$
Grammage of coated layer: 10 g/m$^2$
Re-wettable gum adhesion: 25 gF/mm
Ash: 10%
Opacity: 80%

Embodiment Method

Once the coating machine used to apply the re-wettable gum is started up to reach the established machine conditions, the reel of paper is placed on the unwinding shaft and the web of paper is distributed in the machine circuit, the gum slip is metered into the tray for feeding the cylinders in contact with the paper and the gumming process begins according to the established machine conditions until finishing the reel. After the gumming process, the reel of paper is cut to the format necessary for the subsequent process for sheet or reel printing of the gummed tax stamps or security labels.

Example 10

Use of a Mixture of Mullite Nanoparticles, Cerium Oxide Nanoparticles, Titanium Dioxide Nanoparticles and Bismuth Molibdate Nanoparticles as Security Markers Applied on the Surface in Cellulose Tapes for Insertion into the Security Paper Mass Intended for Printing Legal Tender Notes The characteristics of the nanoparticles mixture are:
Mullite nanoparticles with acicular shape of 50 nm in diameter and 300 nm in length. The nanoparticles are dispersed. The nanoparticles are characterized with a Raman peak at 970 cm$^{-1}$
Cerium oxide nanoparticles, $CeO_2$, with spherical morphology of nm in diameter. The cerium oxide nanoparticles are dispersed and anchor on layered type kaolin microparticles with diameter of 1-2 μm and thickness of 200-400 nm. The cerium dioxide nanoparticles are characterized by a Raman peak at 464 cm$^{-1}$.
Titanium dioxide nanoparticles, $TiO_2$, in the crystalline form of anatase with spherical morphology and average nanoparticles size of 12.5 nm. The titanium dioxide nanoparticles are dispersed and anchor on layered type kaolin microparticles with diameter of 1-2 μm and thickness of 200-400 nm. The titanium dioxide nanoparticles present a main Raman peaks at 143 cm$^{-1}$.
Bismuth molibdate nanoparticles with spherical morphology and 20 nm in diameter in an agglomeration state of 200 nm characterized with two Raman peaks at 712 and 846 cm−1.

The mixtures of nanoparticles comprise 3 wt % of mullite nanoparticlesm, 4 wt % of cerium dioxide, 4 wt % of bismuth molibdate nanoparticles and 2 wt % of titanium dioxide nanoparticles and 87 wt % of kaolin microparticles. In the mixture a dry nanodispersion procedure is adequate to obtain the characteristics of the mixture. The mixture is incorporated in an aqueous media to obtain a suspension of the nanoparticles dispersed on the microparticles with a solid content of 25 wt %.

This example uses a gravure printing machine manufactured by Giave, a gravure cylinder manufactured by Artcyl and etched by Ziraba, natural cellular-based fibrous paper manufactured by Miguel and Costas, gravure ink manufactured by Sicpa and a mixture of the referred nanoparticles in an aqueous solution.

The main characteristics of the installations and materials indicated are described below:
Conditions of the Printing Machine on Each Side of the Paper:
Drying tunnel temperature: 45° C.
Machine speed: 80 m/min
Reel tension: 150 N
Heliofun (antistatic system): 60%
Conditions of the Gravure Cylinder
Type of etching: chemical
Lineature: 90 line/cm
Cell depth: 34 microns
Table: 510 mm
Diameter: 24"=194.02 mm
Conditions of the Ink:
Commercial name of the ink: 67E9011
Viscosity of the ink: 32 s CP4
Viscosity of the varnish for application: 32 s CP4
Main Conditions of the Paper:
Fibrous composition: 100% cellulose
Grammage: 18 g/m$^2$
Thickness: 30 microns
Bendtsen porosity: 144 ml/min
Opacity: 25%
Implementation Method:

Once the printing machine is started up to reach the machine conditions, the gravure cylinder is placed on the unwinding screw and the web of paper is distributed in the machine circuit the ink is mixed with 100 ml of the aqueous dispersion of the referred nanoparticles. Once the perfect dispersion of the components is assured, the content of the drum is pumped to the inkwell of the printing machine. The paper is positioned on the printing cylinder starting the printing of the ink on the paper on one of the sides, controlling the final moisture of the paper, viscosity of the ink and the machine conditions throughout the entire printing process. After the process ends the reel is left at rest for a minimum development time of 24 hours at room temperature (23° C. and 50% RH).

Example 11

Measurement of the Frequency Shift in the Raman Spectrum for a $Co_3O_4$ Based Material in Different Agglomeration States Dispersed $Co_3O_4$ nanoparticles or $Co_3O_4$ nanoparticles with a different agglomeration state were deposited on $Al_2O_3$ particles. Particularly, nanoparticles (known as AlCo1) dispersed on said particles as well as agglomerates of 100 $Co_3O_4$ nanoparticles (AlCo100) were obtained using the method described in application WO 2010/010220. As an additional agglomeration state, $Co_3O_4$ nanoparticles in the original state, i.e., forming agglomerates of several microns in diameter corresponding to an agglomerate formed by thousands of particles were used.

Figure 2:
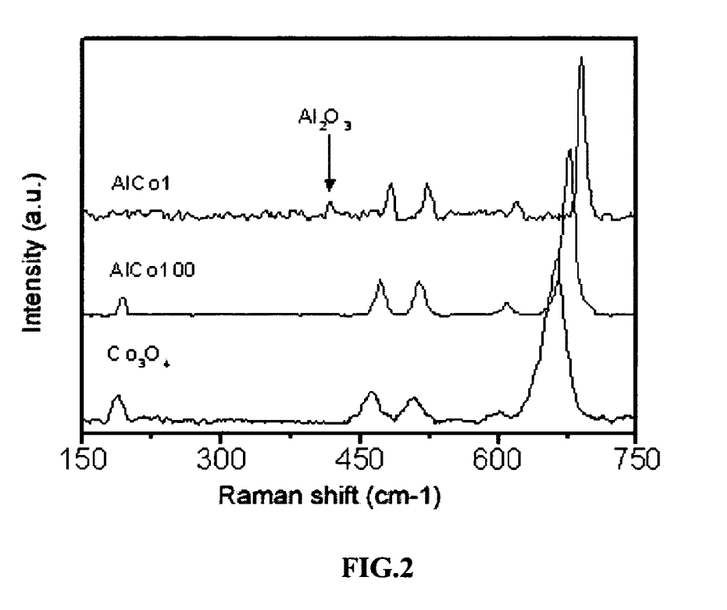
FIG. 2 shows the Raman Spectra of isolated and dispersed $Co_3O_4$ nanoparticles (AlCo1), of agglomerates of a hundred nanoparticles (AlCo100) and of agglomerates of thousands of nanoparticles in their natural state ($Co_3O_4$).

FIG. 2 shows the different spectra obtained for $Co_3O_4$ nanoparticles with a different agglomeration state deposited on $Al_2O_3$ particles. As seen in this figure, upon reducing the size of the agglomerate, the position of the Raman peak is shifted towards higher frequencies while at the same time the peaks become narrower.

Figure 3:
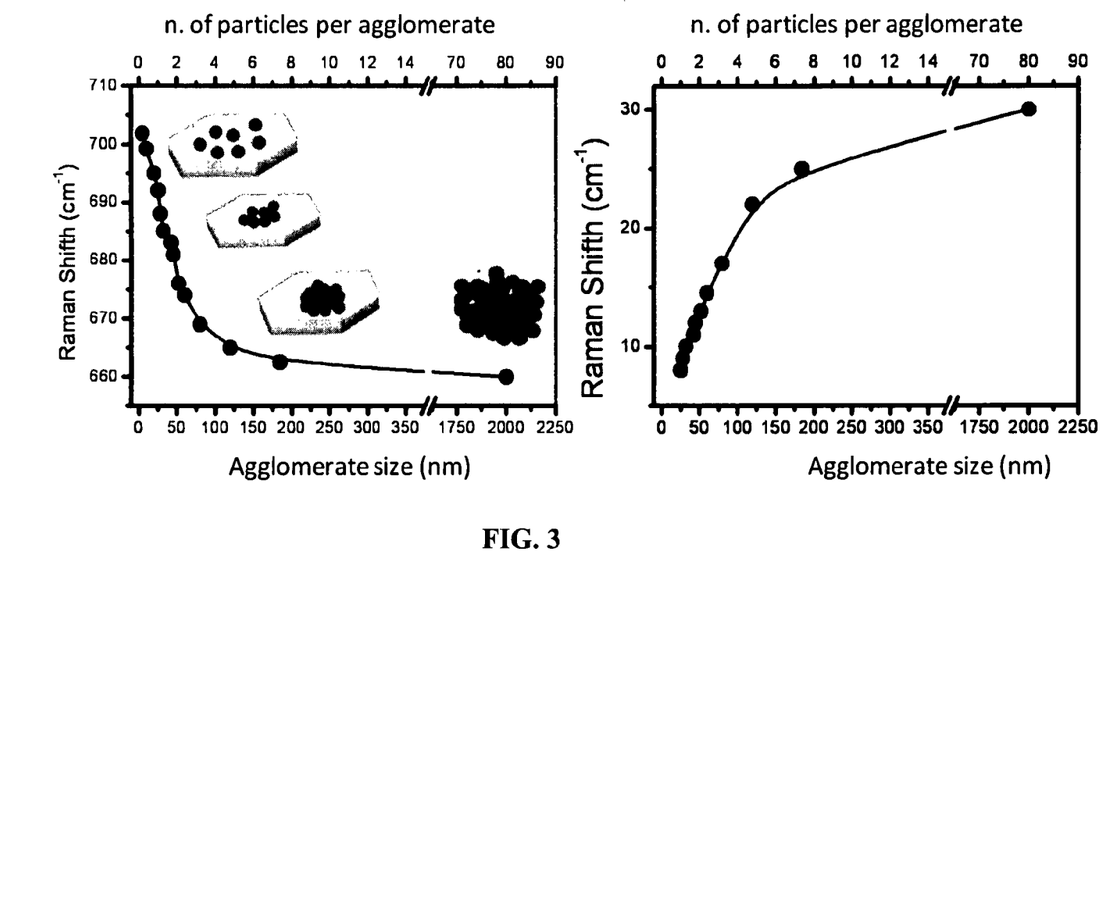
FIG. 3 shows the variation of the position (a) and the width (b) of the main Raman peak of $Co_3O_4$ depending on the agglomeration state thereof.

By studying the variation of the position of the main Raman peak of the $Co_3O_4$ in function of the size of the agglomerate, it can be observed that the Raman shift of said peak is lesser when the size of the agglomerate is larger (see FIG. 3). On the other hand, the width increases with the size of the agglomerate.

Figure 4:
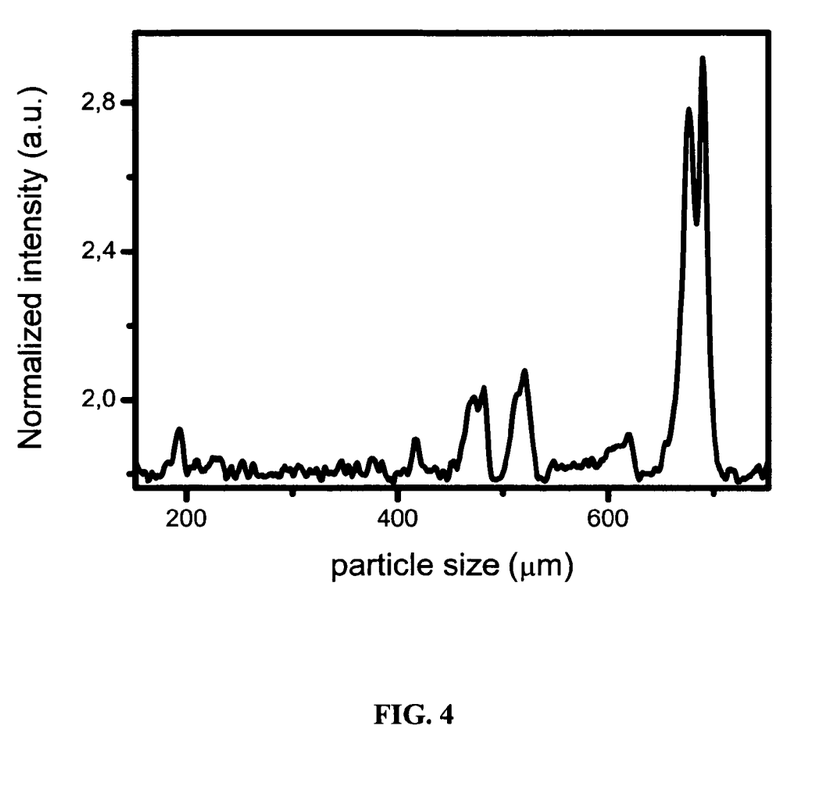
FIG. 4 shows the Raman spectrum corresponding to a 1:1 mixture by weight of isolated, dispersed nanoparticles and agglomerates of 100 $Co_3O_4$ nanoparticles.

If the nanoparticles of this dispersed material are equally mixed with the agglomerates of 100 nanoparticles, a spectrum different from each of the above is observed (see FIG. 4).

A security composition based on a controlled mixture of at least two types of nanoparticles with different agglomeration states which give rise to a particular Raman spectrum depending on the sizes of the agglomerates can thus be defined.

The invention claimed is:

1. A method comprising preparing or labeling a security document, article, or element with a combination comprising at least two types of nanoparticles of material presenting Raman effect, wherein:
   each of the at least two types of nanoparticles is in a dispersed state or is in an agglomeration state forming agglomerates between 2 and 500 nanoparticles where said agglomerates have a size less than 2 microns;
   the at least two types of nanoparticles differ from each other in their chemical composition, in their crystal structure, in their shape, in their size and/or in their dispersed or agglomeration state; and
   when the at least two types of nanoparticles differ in their dispersed or agglomerated state, one type of nanoparticles is in a dispersed state and at least one other type of nanoparticles is in an agglomeration state forming agglomerates of between 2 and 500 nanoparticles, or the at least two types of particles form are in an agglomeration state forming agglomerates containing different numbers of nanoparticles between 2 and 500 nanoparticles.

2. A method according to claim 1, wherein the nanoparticles are deposited on microparticles or on a substrate.

3. A method according to claim 1, wherein the material presenting Raman effect is selected from silicon, $Co_3O_4$, $Ce_2O_3$, $TiO_2$, $X(WO_3)_4$ or $XNbO_3$, where X is selected from alkaline, alkaline-earth, transition metal or lanthanide elements.

4. A method according to claim 1, wherein the at least two types of nanoparticles have the same chemical composition, same crystal structure, same nanoparticle shape, same nanoparticle size, and different dispersion or agglomeration state.

5. A method according to claim 1, wherein one of the at least two types of nanoparticles is in a dispersed state and another of the at least two types of nanoparticles is in an agglomeration state forming an agglomerate comprising between 2 and 500 nanoparticles.

6. A security element, article, or document comprising a combination of at least two types of nanoparticles of materials presenting Raman effect, wherein:
   each of the at least two types of nanoparticles is in a dispersed state or is in an agglomeration state forming agglomerates between 2 and 500 nanoparticles where said agglomerates have a size less than 2 microns;
   the at least two types of nanoparticles differs from each other in their chemical composition, in their crystal structure, in their shape, in their size and/or in their dispersed or agglomeration state; and
   when the at least two types of nanoparticles differ in their dispersed or agglomerate state, one type of nanoparticles is in a dispersed state and at least one other type of nanoparticles is in an agglomeration state forming agglomerates of between 2 and 500 nanoparticles, or the at least two types of particles form are in an agglomeration state forming agglomerates containing different numbers of nanoparticles between 2 and 500 nanoparticles.

7. The security element, article, or document according to claim 6, selected from security paper, security threads, security fibers, security inks, watermarks, tactile effects, cellulose strips, planchettes, holograms, security pigments, security substances, plastic sheets and polymer substrates.

8. The security element, article, or document according to claim 6, comprising a security ink forming part of an image or a code.

9. A security element, article, or document according to claim 6, selected from identification documents, banknotes, cheques, stamps, and stamp-impressed paper, labels and tickets.

10. A method for determining authenticity of a security document, article, or element as defined in claim 6, the method comprising:
    irradiating the security document, article, or element with monochromatic laser radiation; and
    measuring the Raman spectrum of said security document, article, or element to determine the presence of said combination of at least two types of nanoparticles of materials presenting Raman effect.

11. The method according to claim 10, further comprising:
    comparing the measured Raman spectrum with a reference Raman spectrum which corresponds to a security document, article, or element including a combination of at least two types of nanoparticles of materials presenting Raman effect, wherein each of the at least two types of nanoparticles of the security document, article, or element corresponding to the reference Raman spectrum is in a dispersed state, or has a different and pre-determined agglomeration state.

12. A system for determining authenticity of a security document, article, or element as defined in claim 6, the system comprising:
    a positioner where the security document, article, or element is placed;
    a set of lenses which allows focusing the light originating from an incident laser light beam a part of the security document, article, or element to be irradiated;
    a multichannel Raman spectrum detector; and
    a filter for blocking laser radiation that reaches the multichannel detector.

13. The system according to claim 12, further comprising at least one device arranged to compare (i) a Raman spectrum obtained by irradiating the security document, article, or element with monochromatic laser radiation and measuring the Raman spectrum of said security document, article, or element with (ii) a reference Raman spectrum, and arranged to verify whether the security document, article, or element comprises the combination of at least two types of nanoparticles.

14. A method for incorporating a combination of at least two types of nanoparticles of materials presenting Raman effect in a security document or article, wherein each of the at least two types of nanoparticles is in a dispersed state or is in an agglomeration state forming agglomerates between 2 and 500 nanoparticles where said agglomerates have a size less than 2 microns, wherein the at least two types of nanoparticles differ from each other in their chemical composition, in their crystal structure, in their shape, in their size and/or in their dispersed or agglomeration state; and when the at least two types of nanoparticles differ in their dispersed or agglomerated state, one of the type of nanoparticles is in a dispersed state and the at least one other type of nanoparticles is in an agglomeration state forming agglomerates of between 2 and 500 nanoparticles, or the at least two types of particles form are in an agglomeration state forming agglomerates containing different number of nanoparticles between 2 and 500 nanoparticles,
wherein said incorporation comprises one of the following steps (i) to (iii):
(i) incorporating said combination of at least two types of nanoparticles during the manufacturing of the material used to make said security document or article; or
(ii) incorporating said combination of at least two types of nanoparticles as part of an additive which is added to said security document or article; or
(iii) incorporating said combination of at least two types of nanoparticles on a surface of said security document or article.

15. A method according to claim 14, wherein the at least two types of nanoparticles are combined with another constituent to form part of an independent composition that is incorporated into the security document or article according to any one of steps (i) to (iii).

\* \* \* \* \*